(12) United States Patent
Sulakvelidze et al.

(10) Patent No.: US 7,622,293 B2
(45) Date of Patent: Nov. 24, 2009

(54) ***PSEUDOMONAS AERUGINOSA*:** BACTERIOPHAGE AND USES THEREOF

(75) Inventors: Alexander Sulakvelidze, Towson, MD (US); Gary R. Pasternack, Baltimore, MD (US)

(73) Assignee: Intralytix, Inc., Baltimore, MD (US)

( * ) Notice: Subject to any disclaimer, the term of this patent is extended or adjusted under 35 U.S.C. 154(b) by 0 days.

(21) Appl. No.: 11/764,608

(22) Filed: Jun. 18, 2007

(65) Prior Publication Data

US 2008/0311643 A1 Dec. 18, 2008

(51) Int. Cl.
*C12N 7/00* (2006.01)
(52) U.S. Cl. .................................. 435/235.1
(58) Field of Classification Search ........................ None
See application file for complete search history.

(56) References Cited

U.S. PATENT DOCUMENTS

| 2004/0247569 A1 | 12/2004 | Morris et al. |
| 2006/0140911 A1 | 6/2006 | Sharp et al. |

OTHER PUBLICATIONS

Shafer et al., Characterization of *Pseudomonas aeruginosa* Bacteriophage UNL-1, a Bacterial Virus with a Novel UV-A-Inducible DNA Damage Reactivation Phenotype, Applied and Environmental Microbiology, 1999, 65(6):2606-2613.*
Lavigne et al., The structural proteome of *Pseudomonas aeruginosa* bacteriophage ΦKMV, Microbiology, Feb. 2006, 152:529-534.*
Houde et al., Characterization of the *Pseudomonas aeruginosa* Bacteriophage B3: Investigations into the Host Range and Insertion Site, Mar. 2001.*
Kwan, et. al., "Comparative Geonomic Analysis of 18 *Pseudomonas aeruginosa* Bacteriophages", Journal of Bacteriology, vol. 188, pp. 1184-1187, esp. p. 1186, paragraph 4, (Feb. 2006).
Notification of Transmittal of the International Search Report and the Written Opinion of the International Searching Authority, or the Declaration, dated Sep. 29, 2008.

* cited by examiner

*Primary Examiner*—Gary B Nickol
*Assistant Examiner*—Nicole Kinsey White
(74) *Attorney, Agent, or Firm*—Hunton & Williams LLP

(57) ABSTRACT

The present invention is directed to isolated bacteriophage having strong lytic activity against strains of *Pseudomonas aeruginosa*, and methods of using that bacteriophage, and/or progeny or derivatives derived therefrom, to control the growth of *Pseudomonas aeruginosa* in various settings.

4 Claims, 1 Drawing Sheet

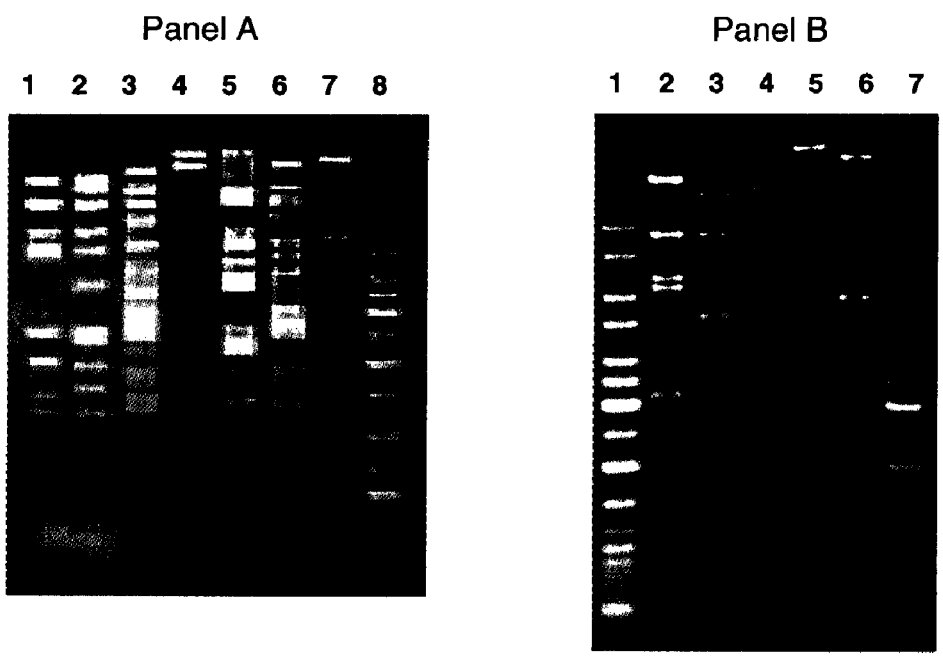
Figure 1. The figure represents RFLP analysis of a Hind III digest of genomic DNA from the indicated deposted bacteriophage. The lanes in Panel A indicate: 1, PAML-20; 2, PAML-14; 3, PAML-13; 4, PAML-5; 5, PAML-4; 6, PAML-3; 7, PAML-2; 8, DNA Ladder Mix (Fermentas). The lanes in Panel B indicate: 1, DNA Ladder Mix; 2, PAML-75; 3, PAML-73; 4, PAML-31-1; 5, PAML-22; 6, PAML-2; 7, DNA Ladder Mix.

PSEUDOMONAS AERUGINOSA: BACTERIOPHAGE AND USES THEREOF

FIELD OF THE INVENTION

The present invention relates to a novel bacteriophage designated PAML-2, PAML-14, PAML-20, PAML-22, PAML-31-1, PAML-73 AND PAML-75 (the "Deposited bacteriophage"), and compositions and preparations corresponding thereto. More specifically, isolated bacteriophage preparations possessing lytic activity against strains of *Psuedomonas aeruginosa* (the "Targeted Bacteria") are provided in order to control the growth of the Targeted Bacteria, which will reduce their ability to contaminate and colonize various environments, including but not limited to (i) raw, unprocessed food products, (ii) equipment used to process or manufacture various food products, (iii) various food products processed or manufactured with equipment contaminated with the Targeted Bacteria, (iv) animals contaminated with the Targeted Bacteria, and (v) animal environments contaminated with the Targeted Bacteria. The invention also provides methods for detecting the presence of the Targeted Bacteria in processed or unprocessed food products, and in equipment used to process or manufacture the food products. In addition, the invention provides methods of using the Deposited bacteriophage to remove the Targeted Bacteria from medical, veterinary, animal husbandry, and other environments where they may be passed to humans or animals. Also, the invention additionally provides methods of using the bacteriophage to prevent and treat animal and human diseases caused by the Targeted Bacteria.

BACKGROUND OF THE INVENTION

Bacteriophages are bacterial viruses that attach to their specific hosts and kill them by internal replication and bacterial lysis involving a complex lytic cycle involving several structural and regulatory genes. Phages are very specific in that they only attack their targeted bacterial hosts. They cannot infect human or other eukaryotic cells. Bacteriophages were first identified, in the early part of the 20th century by Frederick Twort and Felix D'Herelle who called them bacteriophages or bacteria-eaters (from the Greek phago meaning to eat or devour) (Duckworth, D. H. (1976). Who discovered bacteriophage? Bacteriol Rev 40(4): 793-802; Summers, W. C. (1999). Bacteriophage discovered. Felix d'Herelle and the origins of molecular biology. New Haven, Conn., Yale University Press: 47-59). At that time, with the age of antibiotics still in the future, bacteriophages were considered to be a potentially powerful cure for bacterial infections, and they were therapeutically utilized throughout the world during the pre-antibiotic era. The use of phages in humans was found to be very safe; however, phage therapy did not always work and, with the advent of antibiotics that were effective against a broad spectrum of pathogenic bacteria, it gradually fell out of favor in the United States and Western Europe. Several factors (reviewed in more detail in Sulakvelidze, A., Z. Alavidze, et al. (2001). Bacteriophage therapy. Antimicrob Agents Chemother 45(3): 649-659; Summers, W. C. (2001). Bacteriophage therapy. Ann Rev Microbiol 55: 437-51), including the lack of a broad understanding of phage biology and inadequate diagnostic bacteriology techniques, contributed to the failure of some of the early phage therapy studies and to the associated decline of interest in phage therapy in the West. At the same time, phage therapy continued to be utilized in the former Soviet Union and Eastern Europe, where phage therapy still is being used to treat a wide range of bacterial diseases ranging from intestinal infections to septicemia. Comprehensive information about human and veterinary applications of bacteriophages has been recently reviewed by several investigators (Alisky, J., K. Iczkowski, et al. (1998). Bacteriophages show promise as antimicrobial agents. J Infect 36(1): 5-15; Summers, W. C. (2001). Bacteriophage therapy. Annu Rev Microbiol 55: 437-51; Merril, C. R., D. Scholl, et al. (2003). "The prospect for bacteriophage therapy in Western medicine." Nat Rev Drug Discov 2(6): 489-497; Sulakvelidze, A. and P. Barrow (2005). Phage therapy in animals and agribusiness. Bacteriophages: Biology and Applications. E. Kutter and A. Sulakvelidze. Boca Raton, Fla., CRC Press: 335-380; Sulakvelidze, A. and E. Kutter (2005). Bacteriophage therapy in humans. Bacteriophages: Biology and Application. E. Kutter and A. Sulakvelidze. Boca Raton, Fla., CRC Press: 381-436).

Despite the use of bacteriophage in various practical settings, including the treatment of diseases in various animals, there remains in the art a need for the discovery of novel bacteriophages, selection of optimal bacteriophages for specific practical applications, and identifying methods for using these bacteriophages in several critical areas, including clinical applications, food safety-related uses and environmental decontamination. For example, one significant need concerns the treatment of processed or unprocessed food products to reduce, eliminate or prevent colonization with undesirable bacteria such as pathogens responsible for food-borne illness and food spoilage organisms. A second critical area of need concerns the removal of undesirable bacteria from industrial environments such as food processing facilities to prevent colonization thereof. A third critical area of need concerns the removal of antibiotic resistant organisms from environments where they may be passed to susceptible humans and animals, such as hospitals, nursing homes, veterinary facilities, and other such environments. Additionally, new bacteriophage and methods of using the same are needed for the prevention or treatment of animal and human bacterial disease, particularly those diseases caused by antibiotic-resistant organisms.

SUMMARY OF THE INVENTION

The invention meets the described needs and more by providing compositions comprising novel PAML-2, PAML-14, PAML-20, PAML-22, PAML-31-1, PAML-73 AND PAML-75 bacteriophage having lytic specificity for the Targeted Bacteria. The invention additionally provides methods of using the Deposited bacteriophage to control or prevent the infection or colonization of processed and unprocessed food products by Targeted Bacteria, or colonization of equipment involved in the processing of the same food product(s). The invention additionally provides methods of using the Deposited bacteriophage to prevent, eradicate, or reduce the levels of colonization of various animals (including humans) with Targeted Bacteria. The invention also provides methods of detecting the presence of Targeted Bacteria cells on processed or unprocessed food products, or equipment involved in the processing of the same food products. The invention additionally provides methods of using the Deposited bacteriophage for the removal of antibiotic-resistant or other undesirable pathogens from medical, veterinary, animal husbandry, and other environments where they may be passed to humans or animals. The invention additionally provides for methods of using the Deposited bacteriophage to prevent or treat human and/or other animal diseases caused by Targeted Bacteria.

BRIEF DESCRIPTION OF THE FIGURES

Figures

FIG. 1 shows a Restriction Fragment Length Polymorphism (RFLP) profile of the PAML-2, PAML-14, PAML-20, PAML-22, PAML-31-1, PAML-73 AND PAML-75 bacteriophage in comparison to four other bacteriophages also specific for the Targeted Bacteria.

TABLES

Table 1 shows the lytic specificity of the bacteriophage for *Pseudomonas aeruginosa*, the Targeted Bacteria.

DETAILED DESCRIPTION OF THE PREFERRED EMBODIMENTS

Definitions

As used herein, "isolated" will mean material removed from its original environment in which it naturally occurs, and thus is altered by the hand of man from its natural environment. Isolated material may be, for example, foreign nucleic acid included in a vector system, foreign nucleic acid contained within a host cell, or any material which has been removed from its original environment and thus altered by the hand of man. Isolated material further encompasses bacteriophage specific for the Targeted Bacteria or particular Targeted Bacteria isolates, isolated and cultured separately from the environment in which it was located, where these isolates are present in purified compositions that do not contain any significant amount of other bacteriophage or bacterial strains, respectively.

As used therein, "Deposited bacteriophage" will mean isolated bacteriophage PAML-2, PAML-14, PAML-20, PAML-22, PAML-31-1, PAML-73 AND PAML-75 deposited with the ATCC on Apr. 19, 2007, and receiving ATCC Deposit Accession Nos. PTA-8358, PTA-8359, PTA-8360, PTA-8361, PTA-8362, PTA-8363 and PTA-8364.

As used therein, "Targeted Bacteria" will mean *Pseudomonas aeruginosa*.

As used herein, "progeny" shall mean replicates of the Deposited bacteriophage, including descendants of the Deposited bacteriophage created by serial passage of the Deposited bacteriophage or by other means well known in the art, or bacteriophage whose RFLP profiles are substantially equivalent to the RFLP profile of the Deposited bacteriophage (See FIG. 1). The term substantially equivalent is used to describe variability between organisms in accordance with the standards advanced by Tenover et al. from the United States Centers for Disease Control and Prevention (Tenover, F. C. et al. (1995) Interpreting Chromosomal DNA Restriction Patterns Produced by Pulsed-Field Gel Electrophoresis: Criteria for Bacterial Strain Typing. J. Clin. Microbiol. 33:2233-2239). Tenover et al. teaches the acceptable levels of variation that may be seen when the genomes of identical propagated organisms are electrophoretically analyzed following restriction enzyme digestion.

As used herein, "recombinant bacteriophage" shall mean all genetically modified versions of the Deposited bacteriophage or its progeny, obtained by serial passaging (in vivo or in vitro) or genetic manipulations of the Deposited bacteriophage or its progeny. Such manipulations include, but are not limited to, introducing genes or gene cassettes encoding alternative proteins or nonfunctional proteins, or noncoding nucleotide sequences into the genome of the Deposited bacteriophage.

As used herein, "derivatives" shall mean all substances that constitute subunits or expression products of the Deposited bacteriophage or its progeny, including (but not limited to) phage nucleic acids, partial or complete phage genes, gene expression products, and structural components. For example, derivatives of the invention mean polyribonucleotide(s) and polydeoxyribonucleotide(s), including modified or unmodified bacteriophage DNA, cDNA, mRNA and synthetic polynucleotide sequences, as well as DNA/RNA hybrids. Polynucleotides of the invention also encompass modified polynucleotides, such as for example phosphorylated DNAs.

As used herein, "substantially pure" will mean material essentially free of any similar macromolecules or other biological entities that would normally be found with it in nature. For example, a substantially pure bacteriophage is in a composition that contains no more than 1% of other bacteriophages.

As used herein, "bacteriophage composition" will mean a composition comprising, or alternatively consisting essentially of, or alternatively consisting of, the Deposited bacteriophage. A "bacteriophage composition" as used herein does not include the Deposited bacteriophage as it exists in its natural environment prior to isolation and/or substantial purification.

As used herein, "colonization" or "colonized" will refer to the presence of Targeted Bacteria on foodstuff(s), or environmental surface(s), or in vivo such as in the gastrointestinal tract or skin of a mammalian organism without perceptible significant alteration other than the presence of bacteria. The terms "colonization" and "colonized" stand in contrast to the terms "infection" or "infected" which are commonly understood to require perceptible deleterious alteration as part of their definition. "Colonization" and "colonized" may also refer to the presence of bacteria in or on a human or animal without perceptible damage, alteration, or disease.

As used herein, "ATCC" will mean the American Type Culture Collection, located at 10801 University Boulevard, Manassas, Va., 20110-2209, USA.

As used herein, "ORF" will mean an Open Reading Frame which is an in-frame sequence of codons that (in view of the genetic code) correspond to or encode a protein or peptide sequence. Two ORFs correspond to each other if the sequences or their complementary sequences encode the same amino acid sequences. An ORF sequence, operably associated with appropriate regulatory sequences, may be transcribed and translated into a polypeptide in vivo. A polyadenylation signal and transcription termination sequence will usually be located 3' to the coding sequence.

The Deposited Bacteriophage

The Deposited Bacteriophage has binding specificity for Targeted Bacteria, and is capable of lysing Targeted Bacteria. The invention further contemplates variants of the Deposited Bacteriophage, which are bacteriophage having minor variation(s) in the genomic sequence and polypeptides encoded thereby while retaining the same general genotypic and phenotypic characteristics as the Deposited Bacteriophage. Such variants are considered to be the Deposited Bacteriophage in accordance with the standards advanced by Tenover et al. from the United States Centers for Disease Control and Prevention (Tenover, F. C. et al. (1995) Interpreting Chromosomal DNA Restriction Patterns Produced by Pulsed-Field Gel Electrophoresis: Criteria for Bacterial Strain Typing. J. Clin. Microbiol. 33:2233-2239). The invention also contemplates progeny and bacteriophage derivative(s).

The invention contemplates the use of the Deposited Bacteriophage, and its progeny and derivatives, to control the growth on, or colonization of, processed and unprocessed food products by Targeted Bacteria, or the colonization of buildings and equipment, particularly those associated with the processing of the same food product. The invention also provides methods of identifying Targeted Bacteria as a bacterial diagnostic and/or detecting the presence of Targeted Bacteria on processed or unprocessed food products, or equipment or buildings such as those involved in the processing of the same food products. The invention further provides methods of using the Deposited Bacteriophage for the removal of antibiotic-resistant or other undesirable pathogens from medical, veterinary, animal husbandry, or any additional environments where they may be passed to humans or animals. The invention additionally provides for methods of using the Deposited Bacteriophage to prevent and/or treat human and animal diseases caused by Targeted Bacteria. The Deposited Bacteriophage is administered for the methods of the invention as a homogenous phage administration, or alternatively as a component of a multi-phage composition comprising several bacteriophages. These methods of use are provided with greater particularity infra.

Use of the Deposited Bacteriophage and its Progeny

Food Preservation

In one embodiment, the invention contemplates a method for the prevention of foodborne illnesses caused by the Targeted Bacteria, comprising contacting a food product or products with a microbial growth inhibiting effective amount of a bacteriophage composition comprising the Deposited Bacteriophage. The modes of contact include, but are not limited to, spraying or misting the Deposited Bacteriophage composition on the food product(s), or by dipping or soaking the food product(s) in a solution containing a concentration of the Deposited Bacteriophage sufficiently high to inhibit the growth of Targeted Bacteria, or adding, injecting or inserting the Deposited Bacteriophage into the food product(s).

In another embodiment, the invention contemplates the application of the Deposited Bacteriophage composition to equipment associated with the processing of food product(s), such as cutting instruments, conveyor belts, and any other implements utilized in the mass production of food products, including the preparation, storage and packaging steps of food processing. The Deposited Bacteriophage can additionally be introduced into packaging materials used to contain food product(s), prior to or following transfer of the food product(s) to the packaging materials. Alternatively the Deposited Bacteriophage can be useful in the local processing of food products located, for example, in the home or in a restaurant kitchen, using the same modes of contact as described supra.

In another embodiment of the invention, the Deposited Bacteriophage is added as a component of paper products, either during processing or after completion of processing of the paper products. Paper products to which the Deposited Bacteriophage may be added include, but are not limited to, paper towels, toilet paper, moist paper wipes. In a preferred embodiment of the invention, the Deposited Bacteriophage is added as a component of cleansing wipes. The Deposited Bacteriophage may be added in an aqueous state to a liquid-saturated paper product, or alternatively may be added in powder form, such as lyophilized, to dry paper products, or any combination thereof. In similar manner, the Deposited Bacteriophage may be incorporated into films such as those used for packaging foods, such as by impregnating or coating the film.

The methods of the invention further contemplate the application of the Deposited Bacteriophage to the floors, walls, ceilings, drains, or other environmental surfaces in structures such as the industrial food processing, military, or home environments. In a particularly preferred embodiment of the invention, the Deposited Bacteriophage is applied to refrigerated devices used to store or transport food or food products, including but not limited to, home and industrial refrigerators, deli-meat and cheese counters, refrigerated trucks, and mobile food-service vehicles.

In a non-limiting embodiment of the invention, the Deposited Bacteriophage of the invention is useful in preventing the colonization of, or inhibiting the growth of, Targeted Bacteria on processed or unprocessed food products by infecting, lysing or inactivating Targeted Bacteria present on said food product. Processed or unprocessed food products in which the Deposited Bacteriophage is particularly useful in preventing the growth or colonization of Targeted Bacteria include, but are not limited to beef (particularly ground beef), food products made with ground beef such as hamburgers, sloppy joes, lasagna, stews, and other ground beef preparations, fresh vegetables exposed to Targeted Bacteria presumably via animal waste, such as lettuce, spinach, green onions, and other fresh vegetables commonly grown out of doors in fields, drinking water, and foodstuffs secondarily contaminated with Targeted Bacteria through contact with contaminated foods, sewage, or animal feces.

The Deposited Bacteriophage can also be administered to potable and non-potable water sources to reduce or eliminate the presence of Targeted Bacteria.

Bacteriophage compositions of the invention may be provided in aqueous or non-aqueous embodiments for the preservation of food.

Aqueous embodiments of the Deposited Bacteriophage include aqueous compositions comprising, or alternatively consisting of, the Deposited Bacteriophage alone or in combination with other bacteriophage or bacteriophages. Aqueous embodiments of the Deposited Bacteriophage are available in solutions that include, but are not limited to, phosphate buffered saline, Luria-Bertani Broth or chlorine-free water.

Non-aqueous embodiments of the Deposited Bacteriophage include, but are not limited to, lyophilized compositions or spray-dried compositions comprising, or alternatively consisting of, the Deposited Bacteriophage alone or in combination with other bacteriophage(s). Freeze-dried and spray-dried compositions may also include soluble and/or insoluble carrier materials as, for example, processing aids.

The Deposited Bacteriophage can be administered at a concentration effective to prevent the initial colonization of foods with Targeted Bacteria, or to inhibit the growth or colonization of food or food products, as well as the equipment used to process or store food. In a non-limiting embodiment of the invention, the Deposited Bacteriophages typically administered at a growth inhibiting effective amount of a concentration of about $10^7$ to about $10^{11}$ Plaque Forming Units (PFU)/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.). The Deposited bacteriophage at such concentrations may be applied at, for example, about 1 ml/500 cm$^2$ of food surface.

Environmental Control

In another embodiment of the invention, the Deposited Bacteriophage is administered to environments to control the growth or viability of Targeted Bacteria. Environments in which the Deposited Bacteriophage is useful to control the growth or viability of Targeted Bacteria include, but are not limited to, abattoirs, meat processing facilities, feedlots, vegetable processing facilities, medical facilities (including hospitals, out-patient clinics, school and/or university infirmaries, and doctors offices), military facilities, veterinary offices, animal husbandry facilities, public and private restrooms, and nursing and nursing home facilities. The invention further contemplates the use of the Deposited Bacteriophage for the battlefield decontamination of food stuffs, the environment, and personnel and equipment, both military and non-military.

The Deposited Bacteriophage is additionally useful alone or in combination with other bacteriophage(s) and/or other compounds, for preventing the formation of biofilms, or controlling the growth of biofilms, in various environments. Aqueous embodiments of the Deposited Bacteriophage are available in solutions that include, but are not limited to, phosphate buffered saline, Luria-Bertani Broth or chlorine-free water. In a particularly preferred embodiment, the Deposited Bacteriophage is used to control biofilm formation and growth in municipal water systems, industrial water systems, and personal water systems, as well as biofilms present in refrigerated environments.

The modes of administration include, but are not limited to, spraying, hosing, and any other reasonable means of dispersing aqueous or non-aqueous Bacteriophage compositions, in an amount sufficiently high to inhibit the growth or viability of Targeted Bacteria. In a non-limiting embodiment of the invention, the Deposited Bacteriophage is useful in preventing the growth or viability of Targeted Bacteria by infecting, lysing or inactivating Targeted Bacteria present in said environment. Administration of the Deposited Bacteriophage composition includes application to the floors, walls, countertops, ceilings, drains or any other environmental surface.

Bacteriophage compositions of the invention are available in aqueous or non-aqueous embodiments discussed earlier for Food Preservation applications.

In another embodiment of the invention, the Deposited Bacteriophage is added as a component of paper products, either during processing or after completion of processing of the paper products. Paper products to which the Deposited Bacteriophage may be added include, but are not limited to, paper towels, toilet paper, and moist paper wipes. In a preferred embodiment of the invention, the Deposited Bacteriophage is added as a component of cleansing wipes; it may be added in an aqueous state to a liquid-saturated paper product, or alternatively may be added in powder form such as a lyophilized preparation, to dry paper products, or any combination thereof.

The Deposited Bacteriophage can be administered at a concentration effective to inhibit the growth or viability of Targeted Bacteria in a particular environment. In a non-limiting embodiment of the invention, the Deposited Bacteriophage is administered at a concentration of about $10^7$ to $10^{11}$ PFU/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.).

Prevention or Treatment of Infection or Colonization

In another embodiment, the invention contemplates a method for the prevention or treatment of illnesses caused by the Targeted Bacteria, comprising contacting a microbial growth inhibiting effective amount of a bacteriophage composition comprising the Deposited Bacteriophage with a site or sites of infection of a host mammal infected with Targeted Bacteria.

The infected mammalian host may be a human host or animal host. In particular, the host may be a bovine, poultry, or porcine host. Prevention of the infection by Targeted Bacteria, or treatment of infected persons or animals, is particularly preferred in immuno-compromised persons, pregnant females, and newborns and infants, who maybe at an elevated risk of infection by Targeted Bacteria. The modes of contact include, but are not limited to, spraying or misting the bacteriophage composition on the infected mammalian host, by injecting at a site or sites of infection a pharmaceutically acceptable composition containing a concentration of the Deposited Bacteriophage sufficiently high to inhibit the growth of Targeted Bacteria, or by ingesting a solution containing a concentration of the Deposited Bacteriophage sufficiently high to inhibit the growth of Targeted Bacteria. Additional routes of administration include but are not limited to oral, rectal, topical, ophthalmic, buccal, intravenous, otic, nasal, vaginal, inhalation, and intrapleural.

In another nonlimiting embodiment of the invention, the Deposited Bacteriophage is useful for preparing bacterial vaccines or bacterins that eliminate or reduce colonization of the Targeted Bacteria in, and/or their being shed by, various agriculturally-important animals. One example of a practical application for that type of vaccine is in the cattle-raising industry, where its administration may significantly reduce colonization of cattle with the Targeted Bacteria; thus, improving public safety by reducing contamination of beef with the Targeted Bacteria.

Bacteriophage compositions of the invention are available in aqueous or non-aqueous embodiments discussed earlier for Food Preservation applications.

The Deposited Bacteriophage can be administered at a concentration effective to inhibit the growth or viability of Targeted Bacteria in the infected host. In a non-limiting embodiment of the invention, the Deposited Bacteriophage is administered at a concentration of about $10^7$ to $10^{11}$ PFU/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.)

Depending on the severity of peculiarities of the infection, the Deposited Bacteriophage can be administered to animals (including humans) (i) orally, in tablet or liquid formulation ($10^5$-$10^{11}$ PFU/dose), (ii) rectally, (iii) locally (skin, eye, ear, nasal mucosa, etc.), in tampons, rinses and creams, (iv) as aerosols or intrapleunal injections and (v) intravenously.

Use of Recombinant Bacteriophage

In one embodiment of the invention, homologous recombination techniques are used to introduce sequences encoding alternative proteins, non-functional proteins, or non-coding sequences into the bacteriophage DNA sequence. Such techniques are useful to "knock-out" undesired traits of the Deposited Bacteriophage, or alternatively to introduce different traits. In a particularly preferred embodiment of the invention, homologous recombination is used to "knock-out" ORFs encoding proteins that maybe involved in a lysogenic cycle of the bacteriophage.

In another embodiment of the invention, homologous recombination is used to introduce or knock-out genes involved in burst size. For example, homologous recombination is used to introduce alternative bacteriophage genes which delay the burst event or increase the phage burst size. References disclosing alternative bacteriophage genes involved in the timing of the burst event or the size of the phage burst include, but are not limited to (Johnson-Boaz, R., C. Y. Chang, et al. (1994). "A dominant mutation in the bacteriophage lambda S gene causes premature lysis and an absolute defective plating phenotype." Mol Microbiol 13(3): 495-504; Wang, I. N., D. L. Smith, et al. (2000). "Holins: the protein clocks of bacteriophage infections." Annu Rev Microbiol 54: 799-825).

In another embodiment of the invention, recombinant bacteriophage harboring reporter system(s) is generated for various practical applications. One example of possible application of such system is species identification/confirmation of Targeted Bacteria as bacterial diagnostics. Another possible application is the detection of the presence of viable cells of Targeted Bacteria to which the Deposited bacteriophage have specificity. Following the techniques of Loessner et al., for example, one of skill in the art can generate recombinant reporter bacteriophage (Loessner, M. J., C. E. Rees, et al. (1996). "Construction of luciferase reporter bacteriophage A511::luxAB for rapid and sensitive detection of viable Listeria cells." Appl Environ Microbiol 62(4): 1133-1140.). For example, the *Vibrio harveyi* luxAB gene may be introduced into the bacteriophage DNA sequence using techniques such as homologous recombination. An ideal target for the introduction of the luxAB gene is immediately downstream and in frame with an ORF encoding bacteriophage capsid protein, thereby creating a sequence encoding a fusion protein. The preferable location of introduction of the luxAB gene sequence is particularly before any sequence encoding a transcriptional terminator downstream of the ORF encoding a capsid protein. Other bacteriophage ORF sequences which may function as useful sources of luxAB gene-fusions include gene sequences encoding tail-sheath proteins, or any other late gene region sequences encoding phage head or tail proteins. The resulting recombinant bacteriophage may be used with methods of the invention to detect the presence of viable cells of Targeted Bacteria.

In addition to the *Vibrio harveyi* luxAB gene, other reporter genes which are useful for the generation of reporter bacteriophage include, but are not limited to, the firefly luciferase gene.

The invention further contemplates the introduction of one or more of the above-described recombinant events. For example, a recombinant bacteriophage of the invention may harbor one or more reporter gene(s) as well as lack one or more genes associated with certain undesirable biological functions of the bacteriophage.

Use of Bacteriophage Derivatives

Derivatives, such as polypeptides, including but not limited to bacteriophage lytic enzymes, encoded by the bacteriophage or the bacteriophage progeny are used for applications designed to prevent the growth of Targeted Bacteria through cell wall lysis. In this context, lytic polypeptides are useful for the prevention of the growth of Targeted Bacteria on processed and unprocessed food products, as well as equipment used for the processing of said food products.

In another preferred embodiment of the invention, bacteriophage derivatives are useful for the treatment of one or more infections in a mammal, including humans, by administering their therapeutically effective amounts to the patient. This method is useful for the treatment of infections of the gastrointestinal system. Similarly, this method is useful in a prophylactic setting for the prevention of infection by Targeted Bacteria in pregnant mammals, including humans. This method of treatment is further useful for the prevention or other disorders or infections caused by Targeted Bacteria, such as acute bloody or non-bloody diarrhea, sometimes associated with hemolytic-uremic syndrome.

Another nonlimiting embodiment of the invention is that the bacteriophage derivatives such as lysins will be useful for preparing bacterial vaccines or bacterins that eliminate or reduce colonization of the Targeted Bacteria in, and/or their being shed by, various agriculturally-important animals. One example of a practical application for that type of vaccine is in the cattle-raising industry, where administration of such vaccines/bacterins may significantly reduce colonization of cattle with the Targeted Bacteria; thus, improving public safety by reducing contamination of beef with the Targeted Bacteria.

Detection Systems

The Deposited bacteriophage, its progeny, recombinant bacteriophage, or derivatives of the above are useful in methods of screening environmental samples (including food products and food processing equipment) and clinical specimens for the presence of viable cells of Targeted Bacteria. For example, in one such system, recombinant bacteriophage containing a reporter system such as, for example, a luciferase reporter system is applied to the sample and analyzed at some time point in the future for the activation of the reporter molecule. The activation of the reporter molecule is indicative of the presence of viable cells of Targeted Bacteria.

The Deposited bacteriophage, its progeny, recombinant bacteriophage, or derivatives such as lytic enzymes are useful in methods of screening environmental samples including food products and food processing equipment and clinical specimens for the presence of viable cells of Targeted Bacteria, by monitoring and measuring bacterial metabolism products such as bacterial adenosine kinase (AK) or adenosine triphosphate (ATP) released as a result of specific lysis of Targeted Bacteria. For example, when the released ATP is incubated with a luciferin/luciferase mixture, a rapid flash of peak light emission occurs within less than a second, followed by a steady glow lasting for several hours. By measuring the luminescence, it is possible to obtain a quantitative estimate of the number of bacterial cells in a sample. Although the basic approach involved in such detection-based assays is fairly well-established, the existing assays have shortcomings that hinder their wide acceptance. For example, the various reagents that have been used to lyse bacteria and release their ATP have broad-specificity; therefore, ATP is released from all susceptible bacterial and eukaryotic cells present in the sample, which can cause false-positive readings. In this context, the original Deposited Bacteriophage, its progeny, recombinant bacteriophage, or derivatives such as lytic enzymes will specifically lyse Targeted Bacteria without affecting any other prokaryotic or eukaryotic cells that may be present in the sample, thus providing means for accurately and specifically identifying and detecting Targeted Bacteria.

Epidemiological Typing

The Deposited Bacteriophage, and/or its progeny and derivatives may be further useful as a tool for the epidemiological typing of Targeted Bacteria. For example, one of skill in the art can use the Deposited Bacteriophage of the invention to screen a panel of Targeted Bacteria isolates to aid in the taxonomic identification of the Targeted Bacteria, by determining which isolates yield a positive lytic reaction to the Deposited Bacteriophage. For example, see (van der Mee-Marquet, N., M. Loessner, et al. (1997). "Evaluation of seven experimental phages for inclusion in the international phage set for the epidemiological typing of *Listeria* monocytogenes." Appl Environ Microbiol 63(9): 3374-3377.).

Preparation of Vaccines or Bacterins

The Deposited Bacteriophage, and/or its progeny and derivatives, also may be valuable for preparing bacterial lysates to be used as vaccines or bacterins. The immunogenicity of such vaccines or bacterins may be superior to that of so-called dead cell vaccines because phage-mediated lysis is a more effective and gentler approach for exposing protective antigens of bacteria than are approaches used to prepare the latter vaccines. For example, methods commonly used to inactivate bacterial pathogens for dead-cell vaccines, including but not limited to heat treatment, UV-irradiation, and chemical treatment, may deleteriously affect a vaccine's effectiveness by reducing the antigenicity of relevant immunological epitopes (Holt, M. E., M. R. Enright, et al. (1990). "Immunisation of pigs with killed cultures of *Streptococcus suis* type 2." Res Vet Sci 48(1): 23-27.; Melamed, D., G. Leitner, et al. (1991). "A vaccine against avian colibacillosis based on ultrasonic inactivation of *Escherichia coli*." Avian Dis 35(1): 17-22.; Lauvau, G., S. Vijh, et al. (2001). "Priming of memory but not effector CD8 T cells by a killed bacterial vaccine." Science 294(5547): 1735-1739). The presence of viable bacteriophage may also serve as an additional efficacy-enhancing factor, increasing the effectiveness of a phage lysate via their antibacterial effect on the Targeted Bacteria.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The invention may be practiced in ways other than those particularly described in the foregoing description and examples. The teachings provided herein of the invention can be applied to other purposes, other than the examples described below.

The entire disclosure of each document cited (including patents, patent applications, journal articles, abstracts, manuals, books, or other disclosures) in the Background of the Invention, Detailed Description, and Examples is herein incorporated by reference in their entireties.

TABLE 1

Lytic Specificity of the Deposited Bacteriophage

| | *Pseudomonas* Strains intralytix | | Phages, 10,000 PFU/ml | | | | | | |
|---|---|---|---|---|---|---|---|---|---|
| # | ID | Serotype | PAML-22 | PAML-73 | PAML-75 | PAML-31-1 | PAML-2 | PAML-14 | PAML-20 |
| 1 | Ps1 | *aeruginosa* | − | − | − | − | − | − | − |
| 2 | Ps3 | *aeruginosa* | + | + | − | + | + | + | + |
| 3 | Ps4 | *aeruginosa* | + | + | − | + | + | + | + |
| 4 | Ps5 | *aeruginosa* | + | + | − | + | + | + | + |
| 5 | Ps6 | *aeruginosa* | − | − | − | − | − | − | − |
| 6 | Ps7 | *aeruginosa* | − | − | − | − | − | − | − |
| 7 | Ps9 | *aeruginosa* | + | + | − | − | − | + | + |
| 8 | Ps11 | *aeruginosa* | + | − | − | − | − | − | − |
| 9 | Ps13 | *aeruginosa* | + | + | + | − | + | + | + |
| 10 | Ps14 | *aeruginosa* | − | − | − | − | − | − | − |
| 11 | Ps16 | *aeruginosa* | − | − | − | − | − | + | − |
| 12 | Ps17 | *aeruginosa* | − | − | − | − | − | − | − |
| 13 | Ps18 | *aeruginosa* | + | − | − | + | − | − | − |
| 14 | Ps19 | *aeruginosa* | + | − | − | + | − | − | − |
| 15 | Ps21 | *aeruginosa* | − | − | − | − | − | − | − |
| 16 | Ps22 | *aeruginosa* | + | − | + | − | + | − | − |
| 17 | Ps23 | *aeruginosa* | + | − | − | + | + | − | − |
| 18 | Ps24 | *aeruginosa* | − | + | − | − | − | + | + |
| 19 | Ps25 | *aeruginosa* | − | + | − | − | − | + | + |
| 20 | Ps26 | *aeruginosa* | − | + | − | − | − | + | + |
| 21 | Ps27 | *aeruginosa* | − | − | − | − | − | − | − |
| 22 | Ps28 | *aeruginosa* | − | + | − | − | − | − | − |
| 23 | Ps29 | *aeruginosa* | + | − | − | + | − | + | + |
| 24 | Ps30 | *aeruginosa* | − | − | − | − | − | − | − |
| 25 | Ps31 | *aeruginosa* | − | − | + | + | − | − | − |
| 26 | Ps32 | *aeruginosa* | − | − | + | + | + | − | − |
| 27 | Ps33 | *aeruginosa* | − | − | − | − | − | − | − |
| 28 | Ps34 | *aeruginosa* | + | − | + | − | + | − | − |
| 29 | Ps35 | *aeruginosa* | − | − | − | − | − | − | − |
| 30 | Ps36 | *aeruginosa* | − | − | − | − | − | − | − |
| 31 | Ps37 | *aeruginosa* | − | − | − | − | − | − | − |
| 32 | Ps38 | *aeruginosa* | + | + | − | + | + | + | + |
| 33 | Ps39 | *aeruginosa* | + | + | − | + | + | + | + |
| 34 | Ps40 | *aeruginosa* | − | − | − | − | − | − | − |
| 35 | Ps41 | *aeruginosa* | − | + | − | + | + | + | + |
| 36 | Ps42 | *aeruginosa* | − | − | − | − | − | − | − |
| 37 | Ps43 | *aeruginosa* | − | + | − | − | − | + | + |
| 38 | Ps51 | *aeruginosa* | − | − | − | − | − | − | − |
| 39 | Ps52 | *aeruginosa* | − | + | − | + | − | + | + |
| 40 | Ps53 | *aeruginosa* | − | − | − | + | − | − | − |
| 41 | PS54 | *aeruginosa* | − | − | − | − | − | − | − |

TABLE 1-continued

Lytic Specificity of the Deposited Bacteriophage

| | Pseudomonas Strains intralytix | | Phages, 10,000 PFU/ml | | | | | | |
|---|---|---|---|---|---|---|---|---|---|
| # | ID | Serotype | PAML-22 | PAML-73 | PAML-75 | PAML-31-1 | PAML-2 | PAML-14 | PAML-20 |
| 42 | Ps55 | aeruginosa | + | + | − | − | + | − | + |
| 43 | Ps56 | aeruginosa | + | + | − | − | + | + | + |
| 44 | Ps57 | aeruginosa | − | − | − | − | − | − | − |
| 45 | Ps58 | aeruginosa | − | − | − | − | − | − | − |
| 46 | Ps59 | aeruginosa | + | + | − | − | − | + | + |
| 47 | Ps60 | aeruginosa | − | − | − | − | − | − | − |
| 48 | Ps61 | aeruginosa | − | − | − | − | − | − | − |
| 49 | Ps62 | aeruginosa | − | − | − | + | − | − | − |
| 50 | Ps63 | aeruginosa | − | + | − | − | − | + | + |
| 51 | Ps64 | aeruginosa | − | − | − | − | − | − | − |
| 52 | Ps65 | aeruginosa | + | + | − | − | − | + | + |
| 53 | Ps66 | aeruginosa | + | + | − | − | − | + | + |
| 54 | Ps68 | aeruginosa | − | − | − | − | + | − | − |
| 55 | Ps69 | aeruginosa | − | − | − | − | − | − | − |
| 56 | Ps71 | aeruginosa | − | + | − | − | − | − | − |
| 57 | Ps73 | aeruginosa | − | + | − | + | + | − | − |
| 58 | Ps74 | aeruginosa | − | − | − | − | − | − | − |
| 59 | Ps75 | aeruginosa | − | − | + | − | − | − | − |
| 60 | Ps76 | aeruginosa | + | + | − | + | + | + | + |
| Total 57 | | Positive | 20 | 23 | 6 | 17 | 16 | 21 | 21 |
| | | % | 33.33 | 38.33 | 10.00 | 28.33 | 26.67 | 35.00 | 35.00 |

EXAMPLES

Example 1

PAML-2, PAML-14, PAML-20, PAML-22, PAML-31-1, PAML-73 AND PAML-75 Bacteriophage Isolation The PAML-22, PAML-31-1, PAML-73 and PAML-75 bacteriophage were isolated from PyoPhage and the PAML-2, PAML-14, PAML-20 bacteriophage were isolated from Baltimore Inner Harbor waters using lysis of the Targeted Bacteria to form plaques in bacterial lawns as a means of detecting the presence of bacteriophage having lytic specificity for the Targeted Bacteria. Plaques were harvested, diluted, and re-plated on bacterial lawns through a process of serial enrichment until a single bacteriophage species, or monophage, was obtained as determined by a stable restriction fragment length profile of the bacteriophage DNA. The isolates obtained using the technique recited supra may be cultured using the techniques as set forth herein. The bacteriophage was deposited with the ATCC.

Example 2

Deposited Bacteriophage Concentration

Concentration of the Deposited bacteriophage may be determined using techniques known in the art (Adams, M. H. (1959). Methods of study bacterial viruses. Bacteriophages. London, Interscience Publishers, Ltd.: 443-519.). When a single phage particle encounters a permissive bacterium it will lyse it with the concomitant release of newly formed phage particles. When phages are mixed with host cells and poured in a layer of soft agar on the surface of a nutrient agar plate supporting bacterial growth, the cells will resume growth. In areas where no phages are present the bacteria will grow to stationary phase, forming a smooth opaque layer or lawn in the overlay. In areas where phages are present, phage progeny from each infected bacterium will infect neighboring bacteria, resulting in a growing zone of lysis full of liberated phage which eventually becomes visible to the naked eye as a plaque in the otherwise smooth bacterial lawn. These plaques can be counted, and their number is widely used for expressing phage titer in plaque-forming units or PFU. Using this approach, concentration of the Deposited bacteriophage may be determined. Briefly: (1) Various dilutions of the Deposited bacteriophage preparation are prepared; for example, by mixing 0.1 ml of phage sample with 9.9 ml of sterile LB broth. The samples are gently but thoroughly mixed. 0.5 ml of this mixture (which is a $10^{-2}$ dilution of the original sample) is mixed with 4.5 ml of sterile LB broth ($10^{-3}$ dilution). Several 10-fold dilutions are prepared in a similar fashion; (2) the contents of the tubes (1 ml of various dilutions) are transferred into sterile 10 ml culture tubes and 0.1 ml of host bacterial culture are added. The sample is mixed gently before proceeding immediately to the next step; (3) 3-5 ml of warm (45-50° C.) 0.7% LB agar (top agar) are added. The sample is mixed quickly and very gently. Then, the entire contents of the culture tube are poured onto a plate containing solidified LB agar (bottom agar). The plates are slid in circles a few times on the bench top immediately after pouring; (4) after sitting at room temperature for 10 min to allow the top agar to harden, the plates are inverted and placed into a 37° C. incubator and incubated overnight; (5) the next morning, the number of plaques on the plate with 30-300 individual well spaced plaques are counted and the titer calculated and expressed as PFU/ml of the starting sample.

Example 3

Production of the Deposited Bacteriophage

The Deposited bacteriophage is produced using a culture system. More specifically, strain of the host Targeted Bacteria or other closely-related bacterial species on which the bacteriophage can propagate is cultured in batch culture, followed by inoculation of the bacteriophage at the pre-determined multiplicity of infection (MOI). Following incubation and bacterial lysis, the bacteriophage is harvested and purified and/or concentrated to yield phage progeny suitable for the uses enumerated herein. Purification and concentration procedures included variously processing through filtration system(s), centrifugation (including continuous-flow centrifugation) or other well known bacteriophage purification and concentration techniques (Adams, M. H. (1959). Methods of study bacterial viruses. Bacteriophages. London, Interscience Publishers, Ltd.: 443-519.).

The invention provides compositions comprising active viral particles of the bacteriophage capable of lysing strains of Targeted Bacteria. The concentration of bacteriophage is determined using phage titration protocols. The final concentration of the bacteriophage is adjusted by concentration, if a more concentrated phage composition is desired, via filtration, centrifugation, or other means, or by dilution, if a less concentrated phage composition is desired, with water or buffer to yield a phage titer of $10^6$ to $10^{12}$ PFU/ml, preferably $10^{10}$ to $10^{11}$ PFU/ml. The resulting bacteriophage compositions are generally stored at 4° C.; alternatively, preparations can be freeze or spray-dried for storage, or can be encapsulated and stabilized with protein, lipid, polysaccharide, or mixtures thereof. Upon reconstitution, the phage titer can be verified using phage titration protocols and host bacteria. One of skill in the art is capable of determining bacteriophage titers using widely known bacteriophage assay techniques (Adams, M. H. (1959). Methods of study bacterial viruses. Bacteriophages. London, Interscience Publishers, Ltd.: 443-519.).

Example 4

Application of the Deposited Bacteriophage for Preservation of Food Products

The bacteriophage produced using the methods of the present invention may be dispersed in an appropriate aqueous solution or lyophilized or freeze-dried powder and applied to the surface of food products. Alternatively, the bacteriophage may be included with a cheese culture or other microbially active foodstuff prior to or during processing.

Example 5

Isolation of the Bacteriophage DNA

Bacteriophage DNA, a derivative of the bacteriophage, can be used for various applications such as for preparing DNA-based vaccines, and also for analytical purposes, for identifying the bacteriophage such as RFLP profile determination and comparison. Phage DNA can be isolated using a suitable commercial kit such as the Lambda Mini Kit (Qiagen, Inc.; Valencia, Calif.) or the standard phenol extraction technique. For example, 0.75 ml of phage in phosphate-buffered saline solution at a titer of $10^8$-$10^{11}$ PFU/ml is collected. 10 µl of Proteinase K (20 mg/ml) and 2 µl of RNAse (10 mg/ml) is added, followed by incubation at 37° C. for 30 minutes, and a subsequent incubation at 56° C. for 30 minutes. Following incubation, 75 µl of a mixture of 10% SDS (0.1 ml), 0.5 M EDTA (0.1 ml) and 0.8 ml of water is added and incubated at room temperature for 5 min. 0.75 ml of a phenol:chloroform: isoamylalcohol (25:24:1) solution is mixed well with the sample, followed by centrifugation at 13,000 RPM for five (5) min. Next, the supernatant (approximately 600 µl) is carefully removed and transferred to a clean eppendorf tube. 0.6 ml of chloroform is added to the supernatant, mixed well, and centrifuged at 13,000 RPM for five (5) min. The supernatant is then carefully extracted (approximately 500 µl). Next, 0.1 volumes of 3M sodium acetate (40 ml) is added to the solution, followed by 2.5 volumes of cold 95% ethanol (1 ml) to precipitate the bacteriophage DNA. The solution is allowed to incubate at −20° C. for 1 hour, followed by centrifugation at 13,000 RPM for thirty (30) min. Following centrifugation, the pellet is washed with 1 ml of 70% cold ethanol, and the supernatant is poured from the pellet. The pellet is allowed to air dry, and is then resuspended in 30-300 µl of TE (10 mM tris-HCL, pH=8.0-8.5, 1 mM EDTA).

Example 6

Restriction Fragment Length Polymorphism (RFLP) Profile

RFLP can be used to identify the Deposited bacteriophage or its progeny. The progeny will have a substantially equivalent RFLP DNA profile as the RFLP DNA profile of the original bacteriophage. A reference RFLP profile of the Deposited bacteriophage is shown in FIG. 1. DNA was isolated from the bacteriophage using Qiagen Plasmid Miniprep or Midiprep kits (Valencia, Calif.) according to the manufacturer's directions. The DNA was quantitated by measuring absorbance at 260 nm. Approximately 0.5-1 µg of DNA was digested with an appropriate restriction enzyme (FIG. 1), and RFLP profile was determined on 1% agarose gel after staining with ethidium bromide.

Example 7

Lytic Specificity of the Bacteriophage

Sixty *Pseudomonas aeruginosa* strains were screened for their susceptibility to the bacteriophage by the drop-on-lawn method, also known as the "spot test" method. The strains were streaked onto LB agar plates and incubated at 37° C. overnight. One colony of each strain was inoculated into a separate well of a 96-well microtiter plate containing LB broth and incubated at 37° C. until the OD600 reached 0.2-0.3. One hundred microliters of each strain were mixed with LB soft agar and poured onto an LB agar plate. After the soft agar hardened 10 µl of the bacteriophage were spotted in triplicate onto the plates inoculated with the strains of Targeted Bacteria. Lytic activity was observed after overnight incubation at 37° C. The lytic specificity results are presented in Table 1. Of the sixty *Pseudomonas aeruginosa* strains examined, 37, or 62%, were lysed by one or more of the deposited bacteriophage. The individual phage lysed from 10% to 38% of tested bacterial strains.

Example 8

Detection of Targeted Bacteria in Food Samples

The bacteriophage or its derivative, such as lytic enzyme, produced using the methods of the present invention is used to specifically lyse Targeted Bacteria without affecting any other prokaryotic or eukaryotic cells that may be present in the sample; thus, specifically eliciting their release of measurable bacterial products such as AK or ATP. Briefly: (1) Samples of the food to be analyzed are obtained and suspended in appropriate buffer, (2) The Deposited bacteriophage is added to the suspensions, as a result of which the Targeted Bacteria cells present in the samples are lysed and their ATP is released, (3) A luciferin+luciferase preparation is added to the mixtures, and (5) The mixtures' luminescence is measured within 60 sec, and the results are displayed on a handheld luminometer. It may be possible to establish a correlation between the luminometer readings and the number of Targeted Bacteria cells lysed (in general, the average amount of ATP per bacterial cell is 0.5-1.0 fg; precise correlation between the luminometer readings and the number of Targeted Bacteria cells should be experimentally established). If Targeted Bacteria cells are not present in the food samples analyzed, bacterial lysis and ATP-release will not occur.

Example 9

Preparing Vaccines and Bacterins

One example of utilizing bacteriophages to prepare vaccines and bacterins is to use the lytic Deposited bacteriophage to lyse specific strains of the Targeted Bacteria, which will yield bacterial lysates containing minimally-affected immunological epitopes of the bacteria. The phage may be removed from the final vaccine/bacterin preparation. Alternatively, it may be retained unaltered in the preparation because its lytic activity against Targeted Bacteria that may be present in the mammalian organism being vaccinated may increase the preparation's efficacy. In one preferred embodiment of the present invention: (i) the most prevalent, problematic strains of the Targeted Bacteria are chosen so that the vaccine/bacterin contains the immunological epitopes that are most relevant for protecting against the infection, and (ii) the bacteriophage is kept unaltered in the final vaccine/bacterin, at levels ranging from $10^6$-$10^{10}$ PFU/ml.

Bacteriophage-based vaccines and bacterins also may be prepared by using derivatives of the Deposited bacteriophage to lyse the Targeted Bacteria. An example of the general methodology can be briefly outlined from a recent study (Panthel, K., W. Jechlinger, et al. (2003). "*Helicobacter pylori* ghosts by PhiX protein E-mediated inactivation and their evaluation as vaccine candidates." Infect Immun 71(1): 109-16.) of an *Helicobacter pylori* bacterin. The authors used *E. coli-H. pylori* shuttle plasmid pHel2 and lysis gene e of bacteriophage φX174 to construct *H. pylori* lysis plasmid pHPC38, which they introduced into *H. pylori* strain P79. At a pre-determined time, the authors triggered e gene-expression in order to elicit bacterial lysis, and they found that the lysate protected BALB/c mice against *H. pylori* infection.

What is claimed is:

1. An isolated bacteriophage PAML-2, PAML-14, PAML-20, PAML22, PAML31-1, PAML-73, or PAML-75 deposited under ATCC accession Nos. PTA-8358, PTA-8359, PTA-8360, PTA-8361PTA-8362, PTA-8363, and PTA-8364 respectively and variants thereof, wherein said variants have the same phenotypic characteristics of said bacteriophage and said bacteriophage and variants thereof have the same lytic activity against *Pseudomonas aeruginosa* strains.

2. Isolated progeny of the bacteriophage of claim 1, wherein said progeny have the same phenotypic characteristics of said bacteriophage and have the same lytic activity against *Pseudonionas aeruginosa* strains.

3. A composition comprising at least one of the isolated bacteriophages of claim 1.

4. A composition comprising at least one of the isolated bacteriophages of claim 2.

* * * * *

UNITED STATES PATENT AND TRADEMARK OFFICE
CERTIFICATE OF CORRECTION

PATENT NO. : 7,622,293 B2 Page 1 of 1
APPLICATION NO. : 11/764608
DATED : November 24, 2009
INVENTOR(S) : Alexander Sulakvelidze et al.

It is certified that error appears in the above-identified patent and that said Letters Patent is hereby corrected as shown below:

In the Claims

Claim 1, line 16, please change "PAML22" to --PAML-22--, and "PAML31-1" to --PAML-31-1--.

Claim 1, line 18, please change "PTA-8361PTA-8362" to --PTA-8361, PTA-8362--.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,622,293 B2
APPLICATION NO. : 11/764608
DATED : November 24, 2009
INVENTOR(S) : Alexander Sulakvelidze et al.

It is certified that error appears in the above-identified patent and that said Letters Patent is hereby corrected as shown below:

In the Claims

Column 18, Claim 1, line 16, please change "PAML22" to --PAML-22--, and "PAML31-1" to --PAML-31-1--.

Column 18, Claim 1, line 18, please change "PTA-8361PTA-8362" to --PTA-8361, PTA-8362--.

This certificate supersedes the Certificate of Correction issued June 22, 2010.

Signed and Sealed this

Twentieth Day of July, 2010

David J. Kappos
*Director of the United States Patent and Trademark Office*